US012773235B2

(12) United States Patent
Hong

(10) Patent No.: US 12,773,235 B2
(45) Date of Patent: Oct. 27, 2026

(54) POWER-ASSISTED LIPOSUCTION DEVICE

(71) Applicant: LHBioMed Co., Ltd, Wonju-si (KR)

(72) Inventor: Seong Soo Hong, Yongin-si (KR)

(73) Assignee: LHBioMed Co., Ltd, Wonju-si Gangwon-do (KR)

( * ) Notice: Subject to any disclaimer, the term of this patent is extended or adjusted under 35 U.S.C. 154(b) by 1223 days.

(21) Appl. No.: 17/645,299

(22) Filed: Dec. 20, 2021

(65) Prior Publication Data

US 2022/0211412 A1 Jul. 7, 2022

(30) Foreign Application Priority Data

Jan. 4, 2021 (KR) ........................ 10-2021-0000550

(51) Int. Cl.
*A61B 17/34* (2006.01)
*A61B 17/00* (2006.01)

(52) U.S. Cl.
CPC ............................... *A61B 17/3421* (2013.01); *A61B 2017/00389* (2013.01); *A61B 2017/00415* (2013.01);
(Continued)

(58) Field of Classification Search
CPC ...... A61B 17/22012; A61B 17/320068; A61B 17/3421; A61B 17/3476; A61B 2017/00389; A61B 2017/00398; A61B 2017/00415; A61B 2017/00561; A61B 2017/00734; A61B 2017/00792; A61B 2017/22079; A61B 2017/320069; A61B 2017/32007; A61B 2018/00464; A61B 2217/005; A61B 17/32002; A61B 2017/320028; A61B 2017/00738;
(Continued)

(56) References Cited

U.S. PATENT DOCUMENTS 6,213,971 B1 4/2001 Poole
2004/0073195 A1 * 4/2004 Cucin ..................... A61M 1/84
604/542
(Continued)

FOREIGN PATENT DOCUMENTS

CN 109876201 A 6/2019
KR 10-2010-0136828 A 12/2010
(Continued)

OTHER PUBLICATIONS

Office Action for KR 10-2021-0000550 by Korean Intellectual Property Office dated Oct. 20, 2022.
(Continued)

*Primary Examiner* — Sarah Al Hashimi
*Assistant Examiner* — Jihad Dakkak
(74) *Attorney, Agent, or Firm* — Dinsmore & Shohl LLP; Yongsok Choi, Esq.

(57) ABSTRACT

The present invention relates to a power-assisted liposuction device. The power-assisted liposuction device includes: a handpiece; a motor mounted inside the handpiece and connected with a power source to provide driving force; a reverse cam of which one end is connected to the motor; and a cannula connected to the other end of the reverse cam. The reverse cam converts a rotary motion of the motor into a linear reciprocating motion so that the cannula performs a reciprocating motion when the motor is operated.

4 Claims, 2 Drawing Sheets

(52) U.S. Cl.
CPC ............... *A61B 2017/00561* (2013.01); *A61B 2017/00792* (2013.01)

(58) Field of Classification Search
CPC . A61B 2018/00196; A61B 17/320758; A61M 1/76; A61M 1/80; A61M 1/87; A61M 1/88; A61M 2202/08; A61M 2205/106
See application file for complete search history.

(56) References Cited

U.S. PATENT DOCUMENTS

| | | | | |
|---|---|---|---|---|
| 2012/0029545 | A1* | 2/2012 | Nelson ............... | A61B 17/1659 606/171 |
| 2013/0006225 | A1* | 1/2013 | Cucin ................ | A61B 10/0283 604/542 |
| 2020/0323550 | A1* | 10/2020 | Khouri ................... | A61B 17/32 |

FOREIGN PATENT DOCUMENTS

| | | | |
|---|---|---|---|
| KR | 10-2013-0110171 | A | 10/2013 |
| KR | 10-2015-0054347 | A | 5/2015 |
| KR | 10-1656327 | B1 | 9/2016 |
| WO | 2020/210200 | A1 | 10/2020 |

OTHER PUBLICATIONS

International Search Report for PCT/KR2021/019284 by Korean Intellectual Property Office dated Mar. 30, 2022.

* cited by examiner

POWER-ASSISTED LIPOSUCTION DEVICE

CROSS-REFERENCE TO RELATED APPLICATIONS

This application claims priority to and the benefit of Korean Patent Application No. 10-2021-0000550 filed with the Korean Intellectual Property Office on Jan. 4, 2021, the disclosures of which are incorporated herein by reference in their entirety.

TECHNICAL FIELD

The present invention relates to a power-assisted liposuction device and, more specifically, to a power-assisted liposuction device having a reverse cam for converting a rotational motion into a linear motion.

BACKGROUND

Recently, as the interest in appearance increases, plastic surgery is steadily increasing. The liposuction cases occupy about 14.6% of the entire plastic surgery cases. As the obese population increases and the interest in figure increases, the demand for liposuction is also increasing. It is known that more than 10,000 liposuction cases a year were performed in Korea, and the related market is rapidly increasing even abroad.

The liposuction is one of plastic surgery techniques to suck and remove accumulated skin layers and fat layers for the purpose of weight control and body shape correction.

Suction-assisted lipoplasty (SAL) which is a method for sucking and removing fat through a cannula using negative pressure generated by a vacuum pump is the most representative as the liposuction. Moreover, ultrasound-assisted lipoplasty (UAL) for emulsifying fat through ultrasound to easily suck fat is widely used. Furthermore, power-assisted lipoplasty (PAL) to make suction easy and smooth by moving a cannula during a process of sucking fat is also known.

The power-assisted lipoplasty among the lipoplasty methods can reduce procedure time and greatly reduce physical labor of a user since being capable of easily sucking emulsified fat tissues by making the cannula do a rotary motion or a back-and-forth reciprocating motion using electric power or compressed air pressure. So, recently, the power-assisted lipoplasty has been widely used together with the ultrasound-assisted lipoplasty.

For instance, a prior art discloses a power-assisted liposuction device which rotates a cannula by transferring a rotary motion of a motor to a cannula through a plurality of gears. Furthermore, in the case of the conventional power-assisted liposuction device which makes the cannula do the back-and-forth reciprocating motion, a driving device with a complicated mechanism is used to convert the rotary motion of the motor into the linear reciprocating motion of the cannula.

However, such a conventional power-assisted liposuction device has several disadvantages in that the driving device for the rotary motion or the linear reciprocating motion of the cannula has the complicated structure, and in that the volume and weight of a handpiece are increased. Additionally, if the user uses the device for a long time, the user may feel fatigue and may have difficulty in precisely controlling the device.

Therefore, there is a demand for an improved power-assisted liposuction device which has a simple structure, is lightweight, and allows a user to control it precisely.

SUMMARY

The present invention has been made to solve the above-mentioned problems occurring in the prior art, and it is an object to provide a power-assisted liposuction device which has a simple structure and is lightweight.

It is another object to provide a power-assisted liposuction device capable of effectively sucking fat by implementing a linear reciprocating motion of a cannula with a small size.

To accomplish the above objects, there is provided a power-assisted liposuction device including: a handpiece; a motor mounted inside the handpiece and connected with a power source to provide driving force; a reverse cam of which one end is connected to the motor; and a cannula connected to the other end of the reverse cam. Here, the reverse cam converts a rotary motion of the motor into a linear reciprocating motion so that the cannula performs a reciprocating motion when the motor is operated.

The power-assisted liposuction device according to an embodiment of the present invention further includes a reducer arranged between the motor and the reverse cam and mounted on the motor.

According to an embodiment of the present invention, a central axis of the reverse cam and a central axis of the cannula are arranged on the same line.

According to an embodiment of the present invention, the cannula is connected with a tube for providing suction force to the cannula.

According to an embodiment of the present invention, the tube is connected to the cannula after penetrating the handpiece, and the central axis of the tube is arranged to be parallel with a rotary shaft of the motor.

The power-assisted liposuction device according to an embodiment of the present invention further includes a battery mounted inside the handpiece to function as a power source for providing electric power to the motor.

According to an embodiment of the present invention, the power-assisted liposuction device has a simple structure and is lightweight since converting the rotary motion of the motor into the linear reciprocating motion of the cannula utilizing the reverse cam.

Moreover, the power-assisted liposuction device can implement the linear reciprocating motion of the cannula with a small size and can effectively perform liposuction since implementing desired output through the small-sized motor and reducer.

DETAILED DESCRIPTION

Figure 1:
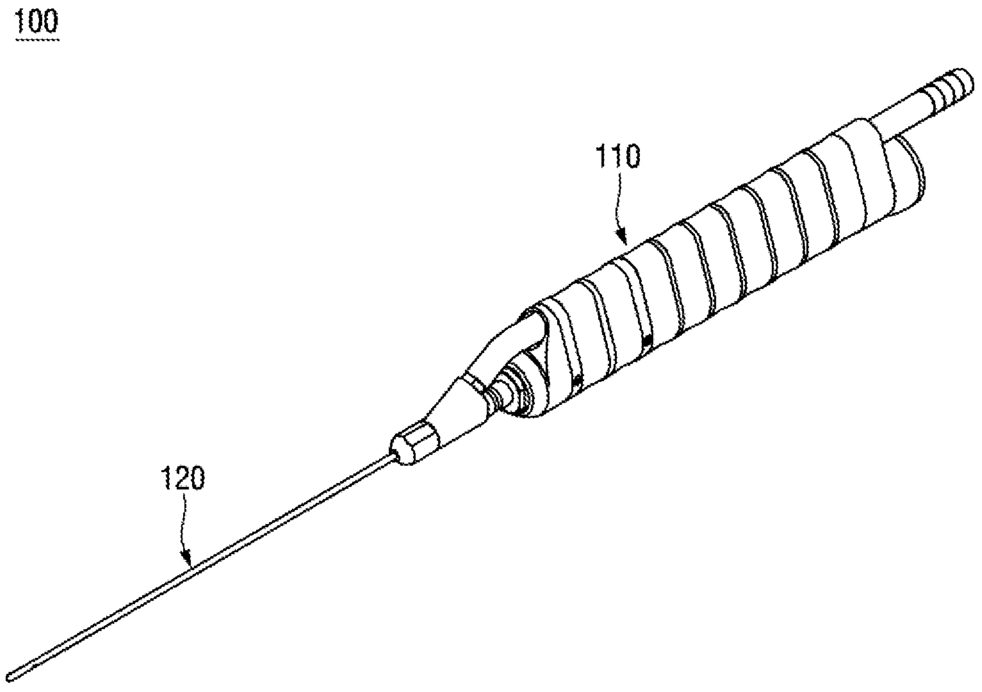
FIG. 1 is a view illustrating a power-assisted liposuction device according to an embodiment of the present invention.

Hereinafter, a preferred embodiment of the present invention will be described in detail with reference to the accompanying drawings.

In order to clearly describe the present invention, detailed descriptions of parts which are not related to the present invention will be omitted, and the same reference numerals are applied to the same components throughout the specification. In addition, since the size, thickness, position, etc. of each component shown in the drawings are arbitrarily shown for convenience of description, the present invention is not limited to the drawings. In other words, it is to be understood that the particular shape, structure, and characteristics described herein can be modified into other embodiments without departing from the spirit and scope of the present invention, and the position or arrangement of the individual components can be varied without departing from the spirit and scope of the present invention.

Accordingly, the following detailed description is not to be construed as a limited meaning, but the scope of the present invention should be taken to encompass all ranges within and equal to the claims.

Figure 2:
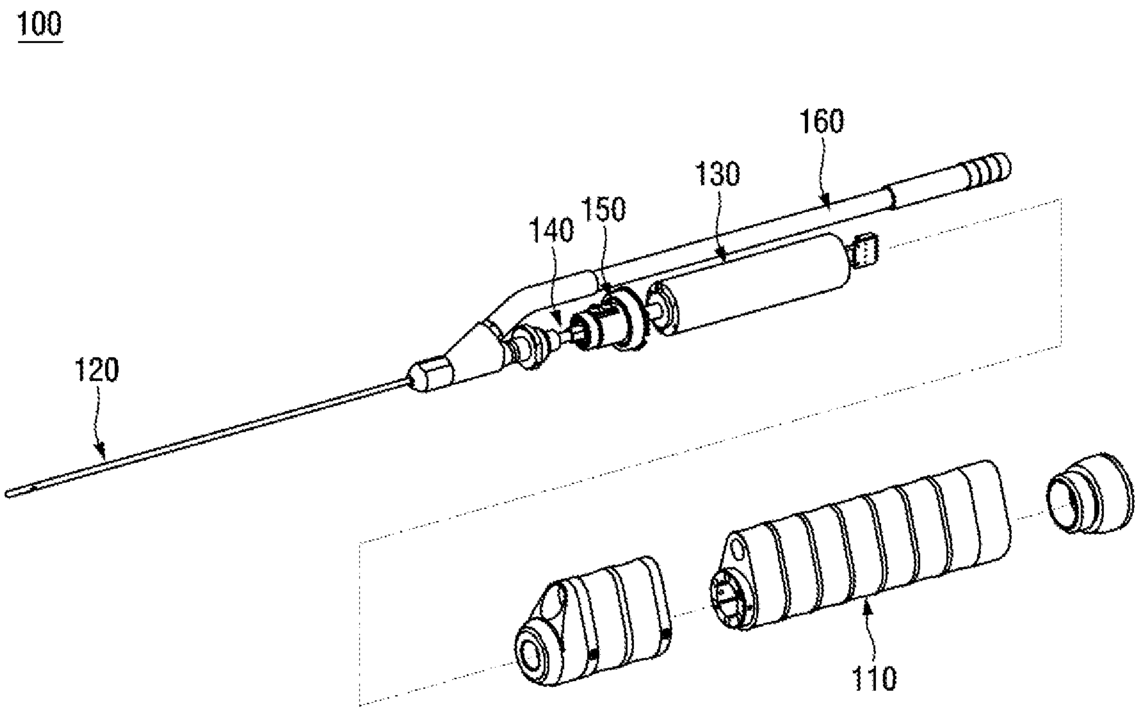
FIG. 2 is a view illustrating an internal structure of the power-assisted liposuction device according to the embodiment of the present invention.

FIG. 1 is a view illustrating a power-assisted liposuction device according to an embodiment of the present invention, and FIG. 2 is a view illustrating an internal structure of the power-assisted liposuction device according to the embodiment of the present invention.

The power-assisted liposuction device 100 according to an embodiment of the present invention is a device for sucking pulverized and emulsified fat tissues by negative pressure after a cannula is inserted into the body, and is capable of efficiently sucking fat tissues by giving vibration, preferably, a back-and-forth reciprocating motion, to the cannula. The power-assisted liposuction device 100 can be used to suck the fat tissues after the fat tissues are pulverized and emulsified by an ultrasound liposuction device (UAL device) or the like.

Referring to FIGS. 1 and 2, the power-assisted liposuction device 100 according to the embodiment of the present invention includes a handpiece 110, a cannula 120, a motor 130, a reverse cam 140, a reducer 150, and a tube 160.

The handpiece 110 according to the embodiment of the present invention corresponds to a part gripped by a user, and has the size and shape which allow the user to grip it with one hand to operate the power-assisted liposuction device 100. The components, such as the motor 130 and the reverse cam 140, to give vibration to the cannula 120 are accommodated in the handpiece 110, and these components are fixedly mounted and can be protected against contact with external environment.

Referring to FIG. 2, the handpiece 110 may be composed of a plurality of cases which are assemblable and disassemblable. For example, the handpiece 110 includes a case for covering the motor 130 and the reducer 150, which will be described later, and a case covering the reverse cam 140, wherein the cases can be assembled to each other and disassembled from each other. Due to the configuration of the handpiece 110, the components accommodated in the handpiece 110 can be maintained well. Meanwhile, the handpiece 110 may be formed of lightweight resin, or may be formed of metal or other known material.

The cannula 120 according to the embodiment of the present invention is inserted into the body to suck the pulverized and emulsified fat tissues, and can be connected to the tube 160 for providing negative pressure. Moreover, as described below, one end of the cannula 120 is connected to the motor 130 and the reverse cam 140 so as to effectively suck fat tissues through vibration, namely, a linear reciprocating motion.

The cannula 120 is an elongated hollow tube, and has a suction port formed at the front end thereof to suck fat tissues. As described above, the suction port is a single hole formed to be slightly spaced from an end portion thereof, and may be varied in size and shape in consideration of the size and function of the cannula 120. For instance, a plurality of the suction ports may be formed in a circumferential direction of the cannula 120. The front end portion of the cannula 120 is formed to have a convex and fluent curve in order to minimize damage of surrounding tissues which may get in contact with the cannula during liposuction.

The motor 130 according to an embodiment of the present invention is mounted inside the handpiece 110 and is connected to a power source (not shown) so as to provide driving force to the cannula 120. As described above, the motor 130 is connected with the cannula 120 by the medium of the reverse cam 140 to provide driving force for the linear reciprocating motion of the cannula 120.

The reverse cam 140 according to an embodiment of the present invention performs a function to convert the rotary motion of the motor into the linear reciprocating motion and transfer the linear reciprocating motion to the cannula 120. For this, one end of the reverse cam 140 is connected with the motor 130, and a cam of the reverse cam 140 is connected to the cannula 120. According to this embodiment, the reverse cam 140 is connected with the cannula 120 through a connection member, and a central axis of the reverse cam 140 and a central axis of the cannula 120 are arranged on the same line. However, the present invention is not limited to the above, and the reverse cam 140 and the cannula 120 may be directly connected with each other. Alternatively, the central axes may be arranged to be spaced apart from each other across the connection member, for example, the central axes are arranged to be parallel to each other.

Figure 3:
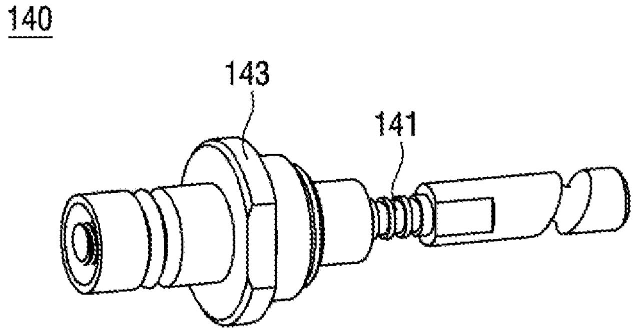
FIG. 3 is a view illustrating a reverse cam of the power-assisted liposuction device according to the embodiment of the present invention.

FIG. 3 is a view illustrating a reverse cam of the power-assisted liposuction device according to the embodiment of the present invention. Referring to FIG. 3, the reverse cam 140 includes a cam 143 moving along a cam shaft 141 of a cylinder type. The cam shaft 141 can rotate in line with rotation of the motor 130, and grooves corresponding to a movement route for the cam 143 are formed on the outer circumferential surface of the cam shaft 141 to cross each other. When the cam shaft 141 is rotated by operation of the motor 130, the cam 143 performs a linear reciprocating motion along the grooves formed on the cam shaft 141. The cam 143 may be connected to the cannula 120 across the connection member so that the rotary motion of the motor 130 is converted into the linear reciprocating motion of the cannula 120 through the reverse cam 140.

Figure 4:
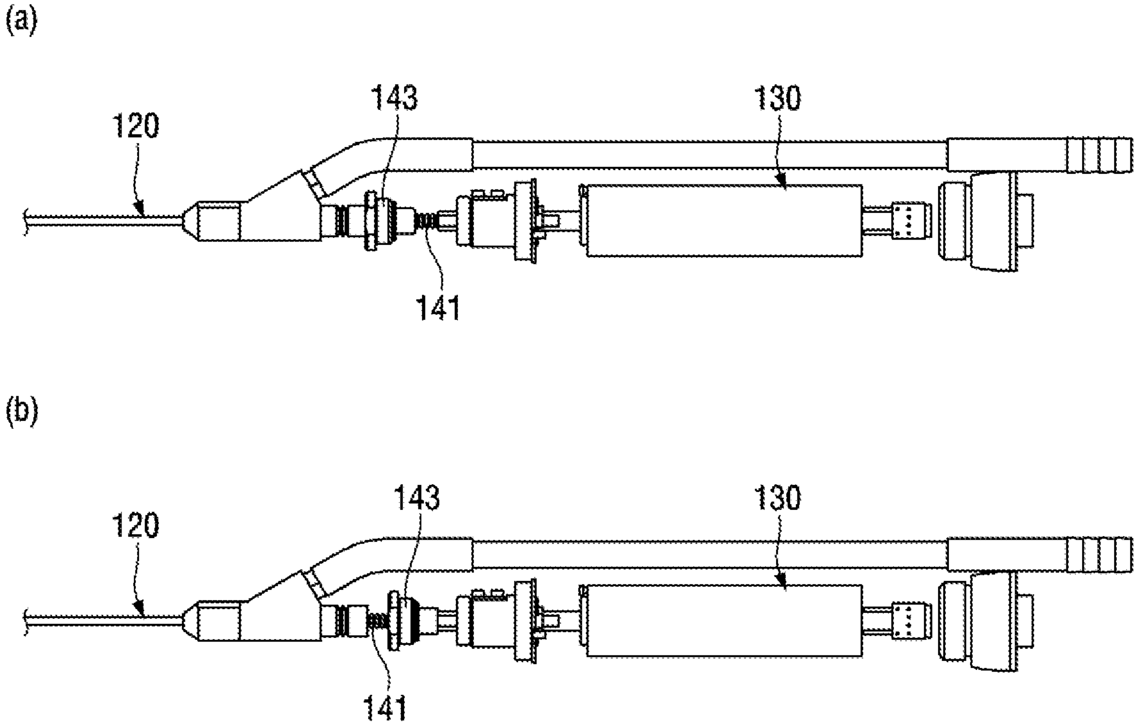
FIG. 4 is a view illustrating an operation of the power-assisted liposuction device according to the embodiment of the present invention.

FIG. 4 is a view illustrating an operation of the power-assisted liposuction device according to the embodiment of the present invention. Referring to FIG. 4, according to the rotation of the motor 130, the cam 143 of the reverse cam 140 performs a reciprocating motion between the left side (FIG. 4(*a*)) and the right side (FIG. 4(*b*)) so that the cannula 120 connected to the cam 143 of the reverse cam 140 also performs the linear reciprocating motion.

The power-assisted liposuction device 100 according to the embodiment of the present invention may further include the reducer 150 arranged between the motor 130 and the reverse cam 140. The reducer 150 is to get high power torque by reducing the number of revolutions when the motor 130 is driven. The reducer 150 can be disposed selectively depending on the use purposes of the power-assisted liposuction device 100, and a reduction gear ratio can be also selected as occasion demands. For instance, in the case of facial liposuction procedure which does not need high power, the reducer is not essential.

Referring to FIG. 2, the cannula 120 according to an embodiment of the present invention is connected with the tube 160 to provide a suction force for sucking fat tissues. The tube 160 is connected with an external suction pump (not shown) so as to suck fat tissues pulverized and emulsified through the cannula 120 by generating vacuum negative pressure from the suction pump.

As illustrated, the tube 160 can penetrate the handpiece 110 and be connected to the cannula 120, and the central shaft of the tube 160 is arranged to be parallel with the rotary shaft of the motor 120. The tube 160 is fixed at the handpiece 110 while penetrating the handpiece 110, thereby preventing movement or separation of the tube 160 to provide suction force stably when the power-assisted liposuction device 100 is used. Of course, the tube 160 may have various structures and arrangements suitable for suction, movement and discharge of fat.

Besides the above, the power-assisted liposuction device 100 according to the embodiment of the present invention may further include a power source for supplying electric power to the motor 130, for instance, a battery (not shown). Of course, the power-assisted liposuction device 100 according to the embodiment of the present invention may not include an internal power supply unit but may be connected to an external power source.

The power-assisted liposuction device 100 according to the embodiment of the present invention can implement the back-and-forth reciprocating motion of the cannula 120 by the coupling structure of the motor 130, the reverse cam 140 and the cannula 120. Furthermore, since the reducer 150 is mounted on the motor 130, even though a small-sized motor is used, the power-assisted liposuction device 100 according to the embodiment of the present invention can provide enough torque for the linear reciprocating motion of the cannula 120.

Therefore, the power-assisted liposuction device 100 according to the embodiment of the present invention is simpler than the conventional power-assisted liposuction device, can implement vibration of the cannula, namely, the linear reciprocating motion in spite of the small size, and can perform more effective liposuction. Additionally, since the inner components of the handpiece are simple, the degree of freedom of the handpiece is increased, and the handpiece has a user-friendly design so as to reduce the user's fatigue caused by long-time use. In addition, the power-assisted liposuction device 100 according to the embodiment of the present invention can reduce manufacturing costs due to the simplified structure of the device.

While the present invention has been described with reference to particular details such as specific elements, the embodiments, and the drawings as described above, this is provided only to help the overall understanding of the present invention and the present invention is not limited to the embodiments. It will be understood by those skilled in the art to which the present invention belongs that various modifications and changes may be made from the description.

Therefore, the spirit of the present invention is not determined by being limited to the above-described embodiments, but the claims described later and all of those that are equivalent to the claims and equivalent modifications thereof belong to the spirit and scope of the present invention.

What is claimed is:

1. A power-assisted liposuction device comprising:
- a handpiece;
- a motor mounted inside the handpiece and connected with a power source to provide driving force;
- a reverse cam of which one end is connected to the motor, the reverse cam including a cam shaft of a cylinder type and a cam moving along the cam shaft;
- a cannula connected to the other end of the reverse cam; and
- a tube connected with the cannular and configured to provide suction force to the cannula,
- wherein a central axis of the reverse cam, a central axis of the cannula and a rotary shaft of the motor are arranged on the same line, while a central axis of the tube is arranged to be spaced apart from and parallel with a rotary shaft of the motor,
- wherein the reverse cam converts a rotary motion of the motor into a linear reciprocating motion so that the cannula performs a reciprocating motion when the motor is operated,
- wherein grooves corresponding to a movement route for the cam are formed on an outer circumferential surface of the cam shaft to cross each other,
- wherein, when the cam shaft is rotated by an operation of the motor, the cam performs a linear reciprocating motion along the grooves formed on the cam shaft.

2. The power-assisted liposuction device according to claim 1, further comprising:
- a reducer arranged between the motor and the reverse cam and mounted on the motor.

3. The power-assisted liposuction device according to claim 1, wherein the tube is connected to the cannula after penetrating the handpiece.

4. The power-assisted liposuction device according to claim 1, further comprising: a battery mounted inside the handpiece to function as a power source for providing electric power to the motor.

* * * * *